US005728390A

United States Patent [19]
Merianos

[11] Patent Number: 5,728,390
[45] Date of Patent: Mar. 17, 1998

[54] COSMETIC COMPOSITION OF AN ALPHA OR BETA-HYDROXY ACID AND A POLYVINYLPYRROLIDONE COMPLEXING AGENT

[75] Inventor: John J. Merianos, Middletown, N.J.

[73] Assignee: ISP Investments Inc., Wilmington, Del.

[21] Appl. No.: 522,781

[22] Filed: Sep. 1, 1995

[51] Int. Cl.$^6$ .............................. A61K 7/02; A61K 9/08; A61K 9/10; A61K 9/14

[52] U.S. Cl. .................. 424/401; 424/69; 424/489; 514/772.3; 514/844; 514/937; 514/944

[58] Field of Search ............................ 424/401, 69, 489; 514/844

[56] References Cited

U.S. PATENT DOCUMENTS

| | | | |
|---|---|---|---|
| 4,900,721 | 2/1990 | Bansemir et al. | 514/25 |
| 5,575,991 | 11/1996 | Kischka et al. | 424/70.2 |

*Primary Examiner*—Thurman K. Page
*Assistant Examiner*—James M. Spear
*Attorney, Agent, or Firm*—Walter Katz; Marilyn J. Maue; Joshua J. Ward

[57] ABSTRACT

What is described herein is a cosmetic composition of an alpha-hydroxy acid, such as lactic acid or glycolic acid, or a beta-hydroxy acid, such as salicylic acid, and a polyvinylpyrrolidone-complexing agent, or derivative thereof, in a suitable solvent, useful for the treatment of skin problems, with only minimal skin irritation for the user.

3 Claims, No Drawings

COSMETIC COMPOSITION OF AN ALPHA OR BETA-HYDROXY ACID AND A POLYVINYLPYRROLIDONE COMPLEXING AGENT

BACKGROUND OF THE INVENTION

1. Field of the Invention

This invention relates to cosmetic compositions, and more particularly, to cosmetic compositions containing an alpha- or beta-hydroxy acid and an anti-irritant agent.

2. Description of the Prior Art

Cosmetic compositions having an alpha- or beta-hydroxy acid as the active ingredient are well known in the art. These compositions are useful for treatment of the skin, particularly for anti-aging, improvement in skin tone, reduction of fine line, enhancement of moisture, and development of a smooth skin. Application of these compositions generally results in a younger-looking skin as new cells replace the old. However, to achieve this improvement in skin condition, it is necessary for the user to tolerate the skin irritation caused by the acid present in the product. Accordingly, skin irritation is a major concern to formulators of compositions of alpha and beta-hydroxy acids, particularly as higher acid levels deliver faster and more effective skin peeling, even though more irritation is perceived by the user as being a more effective treatment.

Accordingly, it is an object of this invention to provide a cosmetic composition of an alpha or beta-hydroxy acid which includes an effective anti-irritant agent therein.

SUMMARY OF THE INVENTION

In this invention, there is described a cosmetic composition including an alpha-hydroxy acid, such as lactic acid or glycolic acid, or a beta-hydroxy acid, such as salicylic acid, and a polyvinylpyrrolidone-complexing agent, or derivative thereof, in a suitable solvent.

DETAILED DESCRIPTION OF THE INVENTION

The cosmetic composition of the invention comprises an alpha-hydroxy acid or a beta-hydroxy acid, and a polyvinylpyrrolidone-complexing agent for the acid. The presence of the PVP-complexing agent in the composition reduces the irritation effect of the acid without affecting its efficacy.

Suitable polyvinylpyrrolidone-complexing agents for use herein include polyvinylpyrrolidone (PVP), and derivatives thereof, such as an alkylated PVP. Preferably the PVP-complexing agent is water soluble. Generally the amount of the PVP-complexing agent in the composition is sufficient to effect a substantial or complete reduction in any skin irritation experienced by the user without affecting the desired improvement in skin condition. This effective amount of PVP may effect a partial or complete complexation of the acid.

The alpha-hydroxy acid of the invention suitably is selected from the group consisting of lactic acid and glycolic acid, and the beta-hydroxy acid is salicylic acid, both as the free acid or salt thereof, and mixtures thereof.

The cosmetic composition or concentrate of the invention may be in the form of a solution, powder, gel or emulsion. As a powder, the composition may contain up to about 10–20% of the acid, while in solution, gel or emulsion form, a lesser amount of the acid may be used, by dilution of the concentrate. In solution, about 1–10% by weight of the acid and 1–10% by weight of PVP is present.

The solvent for the cosmetic composition herein may be water or an organic solvent such as ethyl acetate or ethyl alcohol, and mixtures thereof. The acid itself may be commercially available in aqueous solution only, e.g. lactic acid is sold as an 88% aqueous solution, and it can be used directly in preparing the composition. An organic solvent then may be included during preparation of the composition.

A powder of the composition may be prepared by reacting substantially stoichiometric amounts of the acid and PVP-complexing agent, in a suitable solvent, precipitating the acid-PVP complex from the reaction mixture, and drying.

The invention will be described hereinafter with reference to the following working examples.

EXAMPLE 1

A cosmetic composition was prepared from 12 g of an 88% by weight aqueous solution of lactic acid, 22 g of polyvinylpyrrolidone (PVP-K30), a water soluble form available from International Specialty Products, as PVP-CI, and 300 ml of ethyl acetate. The composition was prepared by forming a suspension of the PVP-CI in ethyl acetate and adding the aqueous lactic acid solution slowly with stirring. The resultant concentrate contains 3.16% by weight lactic acid and 6.6% by weight of PVP. Efficacious skin care products are prepared from the concentrate, are formulated with only minimum skin irritation.

EXAMPLE 2

A powder form of the composition of Example 1 was prepared by following the procedure of Example 1, and, thereafter, precipitating a complex of the lactic acid and PVP, decanting the ethyl acetate, and drying the green precipitate at 50°–60° under vacuum. 23.5 g of a white powder which included 17.4% lactic acid was obtained. The powder then is formulated into efficacious skin care products.

EXAMPLE 3

The procedures of Examples 1 and 2 were repeated using 15 g of salicylic acid in place of lactic acid, 85 g of PVP-CI and 250 ml ethyl acetate. 467 g of a powder which analyzed for 9.5% salicylic acid was obtained. The products also are useful as an efficacious skin care product with only minimum skin irritation.

While the invention has been described with particular reference to certain embodiments thereof, it will be understood that changes and modifications may be made which are within the skill of the art. Accordingly, it is intended to be bound only by the following claims, in which:

What is claimed is:

1. A composition for treatment of skin problems with only minimal skin irritation for the user which consists essentially of about 1–10% by weight of an alpha- or beta-hydroxy acid, or mixtures thereof, and about 1–10% by weight of a polyvinylpyrrolidone-complexing agent, in the form of a powder, or as a solution, gel or emulsion with a solvent selected from the group consisting of water or an organic compound, or mixtures thereof.

2. A composition according to claim 1 wherein the alpha-hydroxy acid is lactic acid or glycolic acid, or mixtures thereof, and the beta-hydroxy acid is salicylic acid.

3. A composition according to claim 1 wherein the pyrrolidone-complexing agent is polyvinylpyrrolidone.

* * * * *